United States Patent [19]

Slingsby et al.

[11] Patent Number: 4,486,312
[45] Date of Patent: Dec. 4, 1984

[54] ANALYSIS OF LIQUID STREAMS USING TUBING WITH PROTUBERANCES ON ITS INNER WALL

[75] Inventors: Rosanne W. Slingsby, Pleasanton; Christopher A. Pohl, Hayward, both of Calif.

[73] Assignee: Dionex Corporation, Santa Clara, Calif.

[21] Appl. No.: 522,826

[22] Filed: Aug. 12, 1983

[51] Int. Cl.³ .............................................. B01D 15/08
[52] U.S. Cl. .................................. 210/656; 210/198.2
[58] Field of Search ..................... 210/635, 656, 198.2; 422/70

[56] References Cited

U.S. PATENT DOCUMENTS

| | | | |
|---|---|---|---|
| 3,522,172 | 7/1970 | Pretorius et al. | 210/635 |
| 3,598,728 | 8/1971 | Bixler et al. | 210/635 |
| 3,784,467 | 1/1974 | Tanimura et al. | 210/635 |
| 4,059,523 | 11/1977 | Mochizuki et al. | 210/635 |
| 4,403,039 | 9/1983 | Ban et al. | 210/656 X |

*Primary Examiner*—John Adee
*Attorney, Agent, or Firm*—Flehr, Hohbach, Test, Albritton & Herbert

[57] ABSTRACT

The constituents of a liquid stream are analyzed by flowing the stream through a hollow tube or fiber with spaced protuberances of a character to disrupt laminar flow and to produce turbulence. In one embodiment, the tubing includes ion exchange sites and is preferentially permeable to one of the ions of an electrolyte. In this manner, the tubing is useful as an electrolyte suppressor in ion chromatography in which the analyte ions are separated by chromatography using the electrolyte and the electrolyte is converted to weakly ionized form by passage through the tubing prior to conductivity detection.

5 Claims, 3 Drawing Figures

U.S. Patent     Dec. 4, 1984     4,486,312
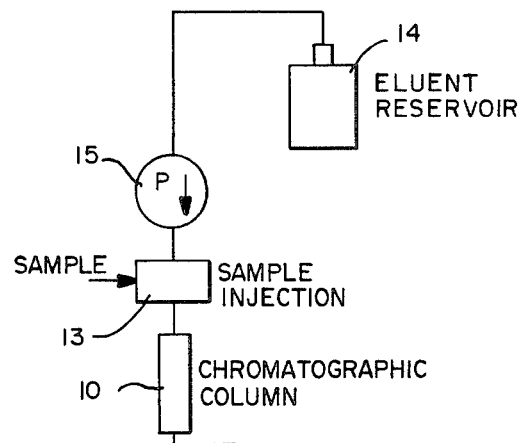
FIG.—1
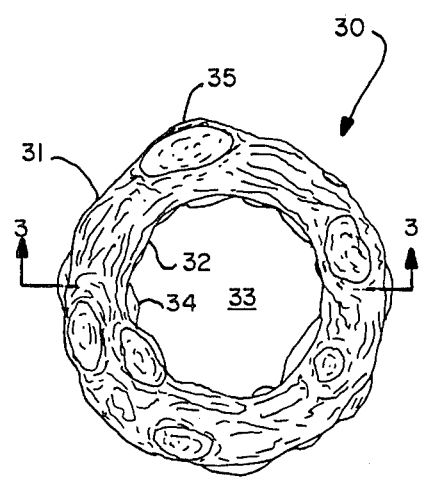
FIG.—2
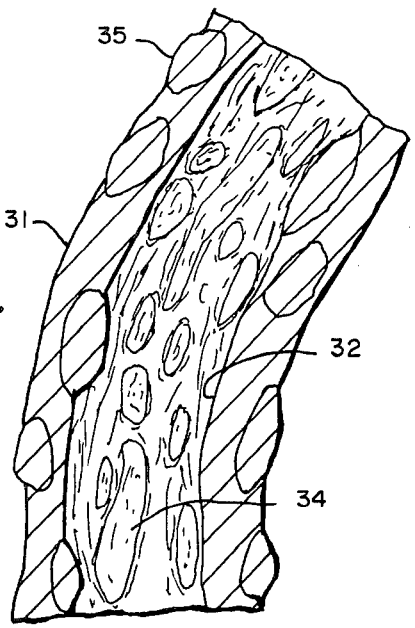
FIG.—3

4,486,312

ANALYSIS OF LIQUID STREAMS USING TUBING WITH PROTUBERANCES ON ITS INNER WALL

BACKGROUND OF THE INVENTION

The present invention relates to method and apparatus for using a particular type of tubing for chemical analysis, preferably as a fiber suppressor in ion chromatography.

Ion chromatography is a known technique for the analysis of ions which typically includes a first chromagraphic separation stage, a second suppression stage, followed by detection, typically by an ion conductivity detector. In the first stage ions of an injected sample are eluted through a separation column using an electrolyte as the eluent. In the second stage, electrical conductivity of the electrolyte is suppressed but not that of the separated ions so that the latter may be determined by a conductivity cell. This technique is described in detail in U.S. Pat. Nos. 3,897,213, 3,920,397, 3,925,019 and 3,296,559.

Suppression or stripping of the electrolyte is described in the above prior art references by an ion exchange resin column. A different form of suppressor column is described in published European patent application No. 32,770 in which a charged membrane, typically in the form of a fiber, is used in place of the resin bed. The sample and eluent are passed through the fiber with a flowing regenerant at the outside wall of the fiber. The fiber comprises an ion exchange membrane partitioning the regenerant from the effluent of chromagraphic separation. The membrane passes ions of the same charge as the exchangeable ions of the membrane to convert the electrolyte of the eluent to weakly ionized form followed by detection of the ions.

One problem with a hollow fiber suppressor system is sample band spreading which degrades the chromatographic resolution. That is, where laminar flow exists, as by the passage of a viscous liquid through a smooth walled fiber, the band of sample broadens or spreads as it flows through the fiber. One way to reduce band spreading is to disrupt the laminar flow by packing of the fiber with beads as described in Stevens, T. S., et al, *Anal. Chem.* 1982, 54, 1206.

One problem with packing of the fiber is that it is labor intensive. Another problem is that the fiber swells or expands under pressure or in contact with solvent during use. This increases the inner diameter of the fiber and permits the beads to concentrate at the outlet end of the fiber. This leaves gaps along the length of the fiber in which there are little or no beads where band spreading can occur. It would be desirable to provide an improved technique for minimizing band spreading which is not as labor intensive as packing of the fibers would be and would eliminate band spreading due to movement of the beads during use.

SUMMARY OF THE INVENTION

In accordance with the invention, tubing (or a fiber) with protuberances, with or without ion exchange sites, (herein "the present tubing") is used to disrupt laminar flow in a liquid chemical analysis. The present tubing may be used in place of the packed fibers of the prior art for minimizing band spreading during ion chromatography. Specifically, the present tubing includes protuberances extending inwardly from the inside wall of the tubing and spaced circumferentially and axially from each other. The protuberances disrupt laminar flow and produce substantial turbulence during passage of the sample stream through the tube. When the present tubing is used as a suppressor for ion chromatography, the wall of the tubing includes ion exchange sites and functions in a similar manner to the fiber suppression described above with the exception that the protuberances can provide a number of advantages. By providing ion exchange sites on the protuberances as well as the wall of the present tubing, the protuberances extend into the center of the flowing stream to increase the surface area available for ion exchange.

The present tubing is useful for creating turbulence in other liquid flow systems for chemical analysis, especially where band spreading is a problem. Thus, for example, the tubing may be used to interconnect portions of an apparatus to minimize band spreading.

BRIEF DESCRIPTION OF THE DRAWINGS

FIG. 1 is a schematic view of apparatus for performing ion chromatography in which the protuberance-containing tubing of the present invention is particularly useful.

FIG. 2 is an end view of tubing in accordance with the present invention.

FIG. 3 is a cross-sectional view taken along the line 3—3 of the tubing of FIG. 2.

DESCRIPTION OF THE PREFERRED EMBODIMENT

The present invention will be described primarily with respect to use of the present tubing in the fiber suppressor portion of a system for the analysis of ionic species by chromatography. First a typical liquid chromatography system will be described followed by a description of the present tubing and its method of formation.

Referring to the liquid chromatography, a liquid sample stream including ionic species is first chromatographically separated by flowing through a chromatographic separation means. Typically, such separation means comprises a separating medium such as ion exchange resin useful for separating ionic species of the sample eluting therethrough using eluent comprising an electrolyte in the solution. The term "liquid chromatography" is intended to include any separation of chemical constituents in a sample liquid on a chromatography medium, such as ion chromatography described in U.S. Pat. No. 3,920,397, and European patent application No. 32,770; ion exclusion chromatography, described in U.S. Pat. No. 4,314,823; mobile phase ion chromatography, described in U.S. Pat. No. 4,265,634; and in Slingsby, R. et al, patent application entitled Method and Apparatus For Mobile Phase Ion Chromatography and Membrane Suppression, filed simultaneously herewith.

The sample stream containing the separated ionic species is then passed through suppressor means comprising the present tubing in an ion exchange membrane form separating the sample effluent flowing within the tubing from means forming a passageway for regenerant at the exterior of the tubing. The present tubing is preferentially permeable to ions of the same charge as the exchangeable ions of the membrane. The exchangeable ions of the membrane are in the ion form necessary to convert the electrolyte of the eluent to a weakly ionized form. In this use, the tubing is referred to as a "fiber", and the method as "fiber suppression".

Referring specifically to the method of fiber suppression, the effluent eluting from the separating medium is passed through the present tubing while the exterior of the fiber is contacted with a flowing regenerant. In one embodiment as set forth in European patent application No. 32,770, ions extracted from the effluent at the ion exchange site of the fiber are diffused through the fiber and are exchanged with ions of the regenerant and are thus diffused ultimately into the regenerant. Exchangeable ions of the ion exchange membrane are in the form necessary to convert the electrolyte of the eluent to a weakly ionized form. Thereafter the resolved ionic species contained in the treated effluent are detected, preferably by a conductivity cell. The detailed description of one ion analysis system and the mechanism of membrane suppression set forth the aforementioned European patent application is incorporated by reference.

Briefly summarized, in one form of membrane suppression, the fiber is formed of a strong-base anion exchange membrane (positively charged) with quaternary ammonium functional groups, typically in the hydroxide ion form. Alternatively, the charged membrane may be a strong-acid cation exchange membrane (negatively charged) with sulphonic acid functional groups, typically in the hydrogen (hydronium) ion form. (The membrane permeates anions while resisting permeation of cations, or vice versa.) Membranes of this type are described in the aforementioned European patent application. Other techniques of fiber suppression to which the present invention is applicable are described in Pohl, C. A., et al, U.S. patent application entitled Method And Apparatus For Ion Analysis And Detection Using Reverse Mode Suppression, and Slingsby et al, U.S. patent application entitled Method And Apparatus For Mobile Phase Ion Chromatography And Membrane Suppression, both filed simultaneously.

As set forth above, an important aspect of the present invention is the use of tubes containing protuberances in place of the aforementioned fiber suppressors or the packed fiber suppressors described in the aforementioned Stevens article. The protuberances of the present tubing extend inwardly from the inside wall of the tube and are spaced both circumferentially and axially. They are of a character to disrupt laminar flow and to produce substantial turbulence during passage of a liquid stream through the tube. The precise configuration, size and spacing of the protuberances required to produce this type of flow are dependent upon a number of factors including the viscosity and velocity of the liquid stream and the i.d. (internal diameter) of the fiber itself. As set forth above, a significant advantage of producing turbulence by radial mixing is to minimize band spreading or broadening of the chromatographically separated constituents in the liquid steam flowing through the tube.

In the fiber suppression mode of the present invention, the tube wall and interior protuberances include ion exchange sites on their surfaces so that the sample liquid stream which passes through the wall of the tube is preferentially permeable to ions of the same charge as the exchangeable ions of the exchange sites. In this manner, the electrolyte may be converted to a weakly ionized form. By way of example as set forth in the above European patent application, a dilute sulfuric acid and water may be used as the regenerant and sodium hydroxide as the electrolyte of the eluent. The ion exchange fiber may be a sulfonated fiber allowing sodium ion to permeate out of the fiber and hydrogen ion to permeate in. Hydroxide and sulfate ions tend not to permeate the fiber wall because of Donnan Exclusion forces. Thus the sodium hydroxide stream is converted to deionized water and the sodium ions permeate the wall of the membrane and are dispersed in the regenerant and removed as $NaHSO_4$ and $Na_2SO_4$. Details regarding the protuberance containing tubing of the present invention and the formation will be described below.

Referring to FIG. 1, a schematic of ion chromatography system for which the present invention is applicable is illustrated. The system includes a chromatographic separation means comprising a chromatographic column 10 which is packed with an ion exchange separating medium, typically in the form of an ion exchange resin bed. Ion separation is performed by eluting a sample through using an eluent which contains electrolyte.

Suppressor means 11 is arranged in series with column 10 for suppressing the conductivity of the electrolyte and the eluent, but not the conductivity of the separated ions. Suppressor means 11 includes the present tubing or fiber as illustrated in detail in FIGS. 2 and 3 described below.

The effluent from suppressor means 11 is directed to a detector for detecting the resolved ionic species eluting therefrom, preferably in the form of a flow-through conductivity cell 12. A suitable sample is supplied to sample injection valve 13 which is swept through the apparatus by a solution of eluent from eluent reservoir 14 drawn by pump 15, and then is passed through the sample injection valve 13. The solution leaving column 10 is directed to suppressor means 11 wherein the electrolyte is converted to a weakly ionized form. The effluent with separated ionic species is then treated by suppressor means 11 and passed to conductivity cell 12. In conductivity cell 12, the presence of ionic material produces an electrical signal proportional to the amount of ionic material. Such signal is typically directed from the cell 12 to a conductivity meter, not shown, thus permitting detection of the concentration of separated species.

The suppressor means may include a reservoir or a regenerant source 16, a chromatographic pump 17, and an ion exchange membrane device 18. Conduits are provided between the reservoir pump and membrane device to deliver regenerant to the latter. Instead of using pump 17, gravity flow or a static reservoir of regenerant may be used.

A suitable membrane device is supplied by Dionex Corporation, Sunnyvale, CA, under the designation Cation Fiber Suppressor (Part No. 35352). Briefly summarized, the membrane device comprises a central core 19 around which the present tubing, designated fiber 20, is wound in a coil of a sufficient number of times (e.g. 6 feet) to provide adequate contact with the fiber walls for permeation of ions between the regenerant and sample. A shell 22 encloses core 19 and forms therewith a regenerant passageway or chamber 23. The chamber receives regenerant through regenerant inlet 24, and the regenerant is discharged to waste through regenerant outlet 26. Column effluent flows through fiber 18 downwardly from membrane inlet 27 through the coil and out membrane outlet 28.

In operation, suppressor means 12 operates by receiving the effluent from the separating column 10 which flows through the interior of the fiber of membrane device 18. Simultaneously, solution from reservoir 16 is pumped in a generally counterflow direction into regenerant inlet 24 and removed from regenerant outlet 26 to waste. The electrolyte component of the eluent is thus neutralized by ion exchange reaction with the fiber wall while the fiber wall is continuously regenerated by the counterflowing regenerant.

In the environment of fiber suppression, the present invention resides in the use of a particular type of fiber or tube. A suitable fiber or tubing is illustrated in FIGS. 2 and 3. Such tubing 30 includes an outer wall 31, and inner wall 32, the interior of which defines a flow through passage 26. Spaced inner protuberances 34 project inwardly along the inner wall of tubing 30 while outer protuberances 35 project outwardly along the outer wall of tubing 25. Protuberances 34 provide the main functional advantages of the present invention, while protuberances 35 are present primarily because of the manner of formation rather than providing the distinct functional advantages of protuberances 27. One advantage of protuberances 35 is that the increased surface area on the regenerant (outer) wall of the fiber allows increased efficiency of the regenerant process.

As set forth above, one important feature of the protuberances is that they disrupt laminar flow along the tube walls to create turbulence and thereby minimize band spreading of the sample. The size and spacing of the protuberances to accomplish this objective cannot be defined with precision. In general, there is a direct relationship between tubing i.d., the size and frequency of protuberances and the tubing, the efficiency of the ion exchange process within the tubing and the magnitude of band spreading. This relationship is that as the tubing i.d. decreases, the protuberances need not be as large and may be spaced farther apart while achieving the same ion exchange efficiency and band character. It is believed that the protuberances improved the efficiency of ion exchange by increasing turbulence and minimizing the time required for an ion in the center of the flow path to reach the wall of the tube. Also, such protuberances are believed to improve the efficiency of the ion exchange by providing ion exchange sites within the wall of the tube to thereby facilitate ion transfer by site-to-site ion transfer.

Suitable size and spatial arrangement for tubing according to the present invention have been approximated as set out below. However, it should be understood that all parameters are coordinated to provide the desired objective of turbulence. With this in mind, suitable specifications for the tubing of the present invention are as follows. The amplitude of the protuberance, that is, the distance from the tube i.d. to the inside of the protuberance for the distance that it protrudes to the inside of the tube, is typically on the order of 2.5 microns to 500 microns and preferably from 25 microns to 125 microns. Another factor is the frequency, that is, the distance between protuberances along the length of the tube. Suitable frequencies are on the order of 25 microns to 1250 microns, preferably 150 microns to 1000 microns. Another factor is the radius of the protrusion, defined as one half its width. Suitable radii are from 2.5 microns to 250 microns, preferably from 25 microns to 75 microns. Another factor is the fiber i.d., measured as the maximum distance between inside walls excluding protuberances. A suitable fiber i.d. range is from 100 microns to 2500 microns and preferably 300 microns to 625 microns.

The formation of tubes with protuberances was found during an experimental program in which a search was made for fibers which were relatively stable in the presence of organic solvents. The procedure employed was to take a commercially available tubing of a suitable internal diameter and to functionalize it with ion exchange sites. One such product is used as intravenous tubing for hospitals such as supplied under the tradename Microline by Thermoplastic Scientifics, Inc. of Warren, N.J. This product is a copolymer of 91% ethylene and 9% vinyl acetate, dimensions 0.011 inch i.d. with an o.d. of 0.024 inch. The technique devised was to first graft a monomer onto this tubing which renders it suitable for conversion to an ion exchange form and thereafter to convert it. Specifically, a vinyl benzyl chloride monomer was used as the grafting monomer which was subsequently aminated. Unexpectedly it was found that under certain conditions the tubing with protuberances useful for the present invention was formed.

A suitable procedure for forming such tubing which was found in the above development program constituted irradiation grafting of a monomer on to an appropriate polymer under conditions to form the protuberances. In one specific procedure, the above ethylene vinyl acetate co-polymer is utilized as the base polymer. Under irradiation, the copolymer is activated for grafting of appropriate monomers. Suitable monomers to be grafted include styrene or vinyl benzyl chloride. For grafting, the tubing constituting the base polymer may be placed into a solution of the monomer in appropriate organic solvents such as methylene chloride and the grafting takes place by irradiation. Suitable concentrations of monomer and solvent range from 32 to 70% and preferably 45 to 55%. An appropriate irradiation dose is 10,000 rad/hour of gamma rays at a time of 72 hours to 400 hours, preferably 120 hours to 200 hours, and a temperature of 80 to 90 degrees F. under an inert atmosphere such as nitrogen. By immersing the entire tube in solvent/monomer solution during grafting, the protuberances are formed on both the inside wall and outside walls as illustrated in FIGS. 2 and 3.

One theory as to why the protuberances are formed is as follows. As the momomer is grafted onto the base polymer network, steric constraints will cause the grafted polymer chains to bend. Since the monomer is relatively insoluble in the base polymer, as grafting proceeds a phase separation occurs. Crystalline and amorphous areas form in the polymer and the polymer backbone bends to accommodate the bulky grafted polymer as polymerization proceeds. By the use of a suitable minimum monomer concentration in the solvent, e.g. at least 40% monomer, protuberances occur in the cation exchange fiber.

Further disclosure of the nature of the present invention is provided by the following specific examples of its practice.

EXAMPLE 1

This example illustrates the formation of the protuberances on the tubing. Fiber tubing is of a type supplied under the name Microline by Thermoplastic Scientifics, Inc. The base polymer is a co-polymer of 91% ethylene and 9% vinyl acetate crosslinked 40 to 65%. The average molecular weight is 190,000 with an average carbon number of 14,200 and a glass transition temperature of greater than 80° C. The dimensions of the tubing are 0.011 inch i.d. by 0.024 inch o.d., plus or minus 0.002 inch.

Tubing of the above type is immersed in a solution of vinyl benzyl chloride in methylene chloride with a concentration of monomer of 45 to 55% by volume. Grafting occurs by irradiating with gamma rays at a dose of 10,000 rad/hour for about 120 to 200 hours at a temperature of 80° to 90° F. in a nitrogen atmosphere. Tubing of a physical character is illustrated in FIGS. 2 and 3 is produced. With the definitions set forth above, the protuberance amplitude range from 25 microns to 125 microns, its frequency from 150 to 1000 mircons, its radius from 25 to 75 microns and a fiber i.d. of 300 microns to 625 microns.

EXAMPLE 2

This example illustrates the functionalizing of the grafted monomer to form an aminated cation fiber suitable for suppression in ion chromatography as set forth above. The monomer employed for grafting is vinyl benzyl chloride.

The grafted tubing is swelled in methylene chloride for ten minutes. The tubing is filled with a solution of 15% weight/weight methyldiethanolamine in methylene chloride. The tubing is aminated by refluxing at 45° C. for 48 hours at a ratio of 20 ml solution per foot of swelled grafted tubing. Then the tubing is washed with methylene chloride and ethanol, air dried and installed in the device of FIG. 1 in six foot coiled lengths.

EXAMPLE 3

In this example, grafted tubing as described in Example 1 is used with the exception that the monomer used for grafting is styrene rather than vinyl benzyl chloride. The percentage of monomer for grafting is 30 to 45%.

The functionalizing of the grafted tubing for cation exchange suppression is performed by the following sulfonation procedure. A grafted tube is swelled in methylene chloride for ten minutes. Then, the tubing is filled with a solution of 3% (w/w) chlorosulfonic acid in methylene chloride. The tubing is sulfonated by soaking the filled tube in this solution for 45 minutes at room temperature at a ratio of 20 ml of the solution per foot of swelled, grafted tubing. Then the tubing is washed in methylene chloride and alcohol and air dried. A 0.5 molar solution of sodium hydroxide at 60° C. is aspirated through the tubing for five minutes. The tubing is soaked in the solution for 15 minutes. The tubing is washed with water and installed in the apparatus of FIG. 1 in coiled form at 6 foot lengths.

EXAMPLE 4

A sample of cations was separated as follows: $Li^+$, 5 ppm; $Na^+$, 5 ppm; $NH_4^+$, 2.5 ppm; $K^+$, 10 ppm; $Rb^+$, 10 ppm; and $Cs^+$, 10 ppm.

The separation mode was ion chromatography in accordance with the system generally described in the aforementioned European patent application using the tubing of Example 2 and the Cation Fiber Suppressor of Dionex. The specific separator column was Dionex column HPIC-CS1 (4 mm i.d. ×200 mm).

The eluent was 5 mM HCl at a flow rate of 2.3 ml/min. The regenerant was 20 mM tetramethylammonium hydroxide at a flow rate of 3.0 ml/min. After the suppressor, the product was detected by an electrical conductivity detector and distinct peaks for the cations were illustrated in a chromatogram.

What is claimed is:

1. In a method for the analysis of constituents in a sample liquid stream, the step of flowing the liquid stream through at least one hollow tube with a wall including protuberances extending inwardly from the inside wall of the tube, said protuberances being spaced both circumferentially and axially and being of a character to disrupt laminar flow and to produce substantial turbulence during passage of the liquid through the tube, said tube wall and protuberances including ion exchange sites on their surfaces, said sample liquid stream including ions of the same charge as the exchangeable ions of said ion exchange sites, said sample liquid stream ions comprising one of the ions of an electrolyte using during liquid chromatography, the wall of the tube being preferentially permeable to ions of the same charge as the exchangeable ions of the ion exchange sites, the exchangeable ions of the ion exchange sites being in the form necessary to convert said electrolyte to a weakly ionized form.

2. The method of claim 1 in which after said liquid stream is flowed through said hollow tube, the separated constituents are detected.

3. The method of claim 2 in which said detecting is performed by measurement in a conductivity cell.

4. Apparatus for the chromatographic separation and analysis of ionic species comprising:
   (a) chromatographic separator means for separating ionic species in the presence of an electrolyte;
   (b) means for directing an eluent containing electrolyte to said chromatographic separation means;
   (c) suppression means communicating with said separation means for treating effluent eluting therefrom, said suppression means comprising at least one hollow tube including protuberances extending inwardly from the inside wall of the tube, said protuberances being spaced both circumferentially and axially, and being of a character to disrupt laminar flow and to produce substantial turbulence during passage of a liquid stream through the tube thereby minimizing band broadening of the separated ionic species, said tube wall and protuberances including ion exchange sites on their surfaces and being preferentially permeable to ions of the same charge as said exchangeable ions of said ion exchange sites, said exchangeable ions being in the form needed to convert the electrolyte of the eluent to a weakly ionized form, and
   (d) detector means communicating with said suppressor means for detecting the ionic species eluting therefrom.

5. The apparatus of claim 4 together with means forming a passageway for regenerant to the exterior of said tube, and means for providing a moving stream of regenerant to said regenerant passageway.

* * * * *